US012599754B2

(12) United States Patent
Matlock et al.

(10) Patent No.: US 12,599,754 B2
(45) Date of Patent: Apr. 14, 2026

(54) GUIDEWIRE ASSEMBLY WITH INTERTWINED CORE WIRE

(71) Applicant: Acclarent, Inc., Irvine, CA (US)

(72) Inventors: George L. Matlock, Laguna Hills, CA (US); Henry F. Salazar, Pico Rivera, CA (US)

(73) Assignee: Acclarent, Inc., Irvine, CA (US)

( * ) Notice: Subject to any disclaimer, the term of this patent is extended or adjusted under 35 U.S.C. 154(b) by 1012 days.

(21) Appl. No.: 17/699,225

(22) Filed: Mar. 21, 2022

(65) Prior Publication Data

US 2022/0370768 A1 Nov. 24, 2022

Related U.S. Application Data

(62) Division of application No. 16/031,275, filed on Jul. 10, 2018, now Pat. No. 11,278,706.

(Continued)

(51) Int. Cl.
*A61M 25/09* (2006.01)
*A61B 1/00* (2006.01)
(Continued)

(52) U.S. Cl.
CPC ........... *A61M 25/09* (2013.01); *A61B 1/0011* (2013.01); *A61B 1/00133* (2013.01); *A61B 1/01* (2013.01);
(Continued)

(58) Field of Classification Search
CPC .... A61M 25/09; A61M 3/0279; A61M 29/02; A61M 25/0102; A61M 25/0113;
(Continued)

(56) References Cited

U.S. PATENT DOCUMENTS 5,067,489 A * 11/1991 Lind ............... A61M 25/09033
600/585
5,282,478 A 2/1994 Fleischhaker, Jr. et al.
(Continued)

FOREIGN PATENT DOCUMENTS

JP 2990199 B2 12/1999
JP 2001-204825 A 7/2001

OTHER PUBLICATIONS

International Search Report and Written Opinion dated Jan. 7, 2019, for International Application No. PCT/IB2018/056771, 12 pages.
(Continued)

*Primary Examiner* — Patrick Fernandes
(74) *Attorney, Agent, or Firm* — Morgan, Lewis & Bockius LLP

(57) ABSTRACT

An apparatus and method of manufacture includes a helical wire coil and a core wire. The core wire has a first wire portion and a second wire portion. The first wire portion of the core wire extends through the helical wire coil. The second wire portion of the core wire is intertwined with the first helical wire coil to fixedly secure the core wire relative to the first helical wire coil. The core wire is formed from a first material that is non-extensible. The core wire is fixedly secured relative to a distal portion of the helical wire coil such that the core wire inhibits longitudinal elongation of the helical wire coil along a longitudinal coil axis.

20 Claims, 8 Drawing Sheets

Related U.S. Application Data

(60) Provisional application No. 62/555,714, filed on Sep. 8, 2017.

(51) Int. Cl.

| | |
|---|---|
| *A61B 1/01* | (2006.01) |
| *A61B 1/07* | (2006.01) |
| *A61B 1/12* | (2006.01) |
| *A61B 1/227* | (2006.01) |
| *A61B 1/233* | (2006.01) |
| *A61B 5/00* | (2006.01) |
| *A61B 5/06* | (2006.01) |
| *A61B 17/24* | (2006.01) |
| *A61B 34/20* | (2016.01) |
| *A61M 3/02* | (2006.01) |
| *A61M 25/01* | (2006.01) |
| *A61M 29/02* | (2006.01) |

(52) U.S. Cl.
CPC ............... *A61B 1/07* (2013.01); *A61B 1/233* (2013.01); *A61B 5/062* (2013.01); *A61B 5/6803* (2013.01); *A61B 5/6851* (2013.01); *A61B 34/20* (2016.02); *A61M 3/0279* (2013.01); *A61M 29/02* (2013.01); *A61B 1/00082* (2013.01); *A61B 1/12* (2013.01); *A61B 1/227* (2013.01); *A61B 17/24* (2013.01); *A61B 2034/2051* (2016.02); *A61M 25/0102* (2013.01); *A61M 25/0113* (2013.01); *A61M 25/09041* (2013.01); *A61M 2025/09083* (2013.01); *A61M 2025/09091* (2013.01); *A61M 2025/09116* (2013.01); *A61M 2025/09191* (2013.01); *A61M 2207/00* (2013.01); *A61M 2210/0675* (2013.01); *A61M 2210/0681* (2013.01)

(58) Field of Classification Search
CPC .. A61M 25/09041; A61M 2025/09083; A61M 2025/09091; A61M 2025/09116; A61M 2025/09191; A61M 2207/00; A61M 2210/0675; A61M 2210/0681; A61B 34/20; A61B 1/0011; A61B 1/00133; A61B 1/01; A61B 1/07; A61B 1/233; A61B 5/062; A61B 5/6803; A61B 5/6851; A61B 2034/2051; A61B 1/00082; A61B 1/12; A61B 1/227; A61B 17/24
See application file for complete search history.

(56) References Cited

U.S. PATENT DOCUMENTS

| | | | | |
|---|---|---|---|---|
| 5,415,639 | A | * | 5/1995 | VandenEinde .... A61M 25/0668 604/102.02 |
| 5,551,443 | A | * | 9/1996 | Sepetka ................ A61M 25/09 600/434 |
| 7,720,521 | B2 | | 5/2010 | Chang et al. |
| 8,123,722 | B2 | | 2/2012 | Chang et al. |
| 8,190,389 | B2 | | 5/2012 | Kim et al. |
| 8,320,711 | B2 | | 11/2012 | Altmann et al. |
| 8,702,626 | B1 | | 4/2014 | Kim et al. |
| 9,155,492 | B2 | | 10/2015 | Jenkins et al. |
| 9,167,961 | B2 | | 10/2015 | Makower et al. |
| 9,198,736 | B2 | | 12/2015 | Kim et al. |
| 9,962,530 | B2 | | 5/2018 | Johnson et al. |
| 10,610,308 | B2 | | 4/2020 | Sema et al. |
| 11,278,706 | B2 | | 3/2022 | Matlock et al. |
| 2002/0169473 | A1 | | 11/2002 | Sepetka et al. |
| 2007/0208252 | A1 | | 9/2007 | Makower |
| 2008/0183128 | A1 | | 7/2008 | Morriss et al. |
| 2010/0030031 | A1 | | 2/2010 | Goldfarb et al. |
| 2011/0004057 | A1 | | 1/2011 | Goldfarb et al. |
| 2011/0015618 | A1 | * | 1/2011 | Satou .............. A61M 25/09016 604/528 |
| 2011/0060214 | A1 | | 3/2011 | Makower |
| 2012/0071857 | A1 | | 3/2012 | Goldfarb et al. |
| 2014/0046302 | A1 | | 2/2014 | Green et al. |
| 2014/0200444 | A1 | | 7/2014 | Kim et al. |
| 2014/0364725 | A1 | | 12/2014 | Makower |
| 2016/0008083 | A1 | | 1/2016 | Kesten et al. |
| 2016/0310042 | A1 | | 10/2016 | Kesten et al. |
| 2016/0310714 | A1 | | 10/2016 | Jenkins et al. |
| 2017/0120020 | A1 | | 5/2017 | Lin et al. |
| 2019/0060618 | A1 | | 2/2019 | Matlock |

OTHER PUBLICATIONS

Japanese Notification of Reasons for Refusal dated May 31, 2022, for Application No. 2020-513729, 5 pages.

\* cited by examiner

GUIDEWIRE ASSEMBLY WITH INTERTWINED CORE WIRE

CROSS-REFERENCE TO RELATED APPLICATION

This application claims priority to Provisional Patent Application Ser. No. 62/555,714 filed on Sep. 8, 2017 entitled "Guidewire Assembly with Intertwined Core Wire," the disclosure of which is hereby expressly incorporated by reference herein, in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Irvine, California.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Irvine, California.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, California.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or Mill, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Irvine, California; systems available from Surgical Navigation Technologies, F Inc., of Louisville, Colorado; and systems available from Calypso Medical Technologies, Inc., of Seattle, Washington.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3-dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
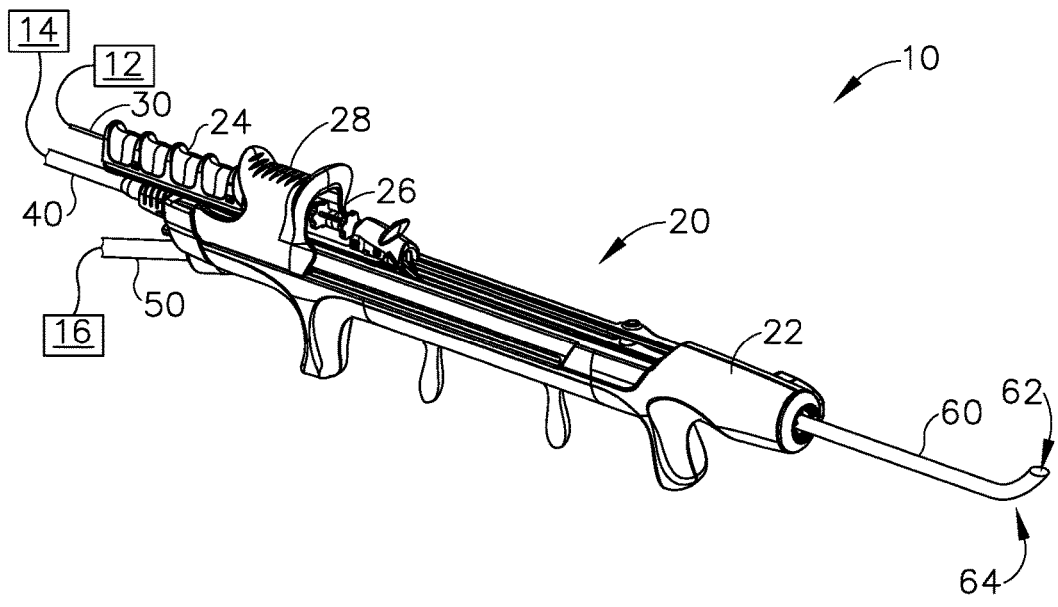
FIG. 1A depicts a perspective view of an exemplary dilation instrument assembly, with an exemplary guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. However, surgical instruments are used in many orientations and positions, and these terms are not intended to be limiting and ab solute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows a first exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) is part of an IGS system as described below with respect to FIGS. 2-3. In some other versions, guidewire power source (12) comprises a source of light as described below with respect to FIGS. 4-6. In the present example shown in FIGS. 1A-1D, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
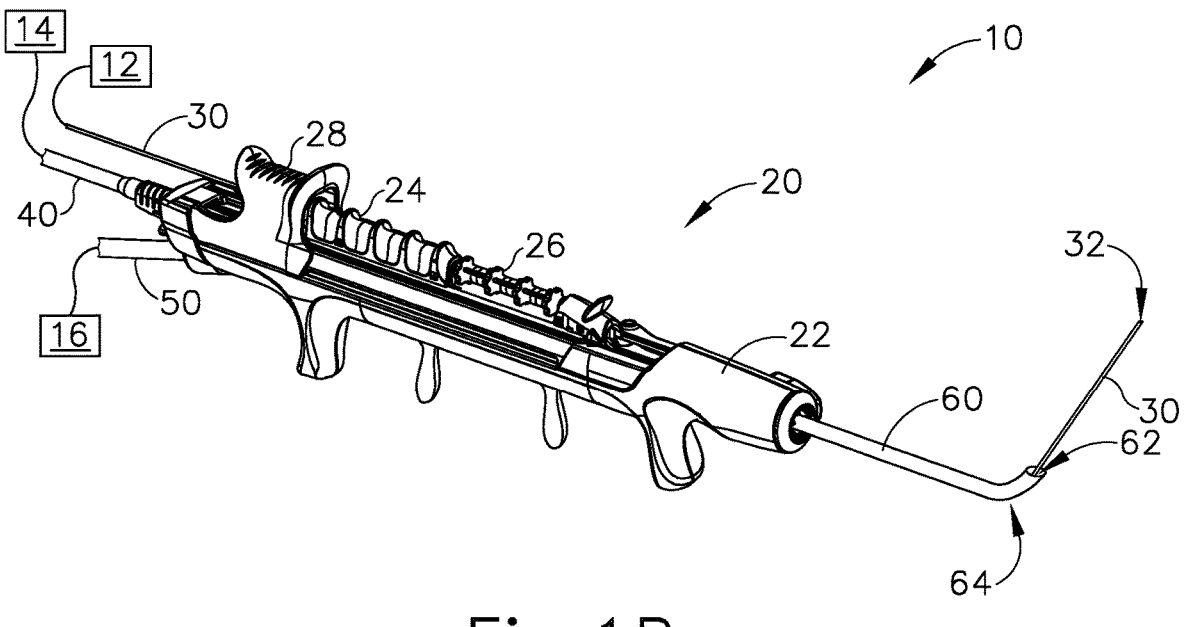
FIG. 1B depicts a perspective view of the dilation instrument assembly of FIG. 1A, with the guidewire in a distal position, and with the dilation catheter in the proximal position.

Dilation instrument (30) further comprises an exemplary guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to a distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32), such as illuminating guidewire (150) (see FIGS. 4-6) discussed below. Optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™ Sinus Illumination System by Acclarent, Inc. of Irvine, California. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
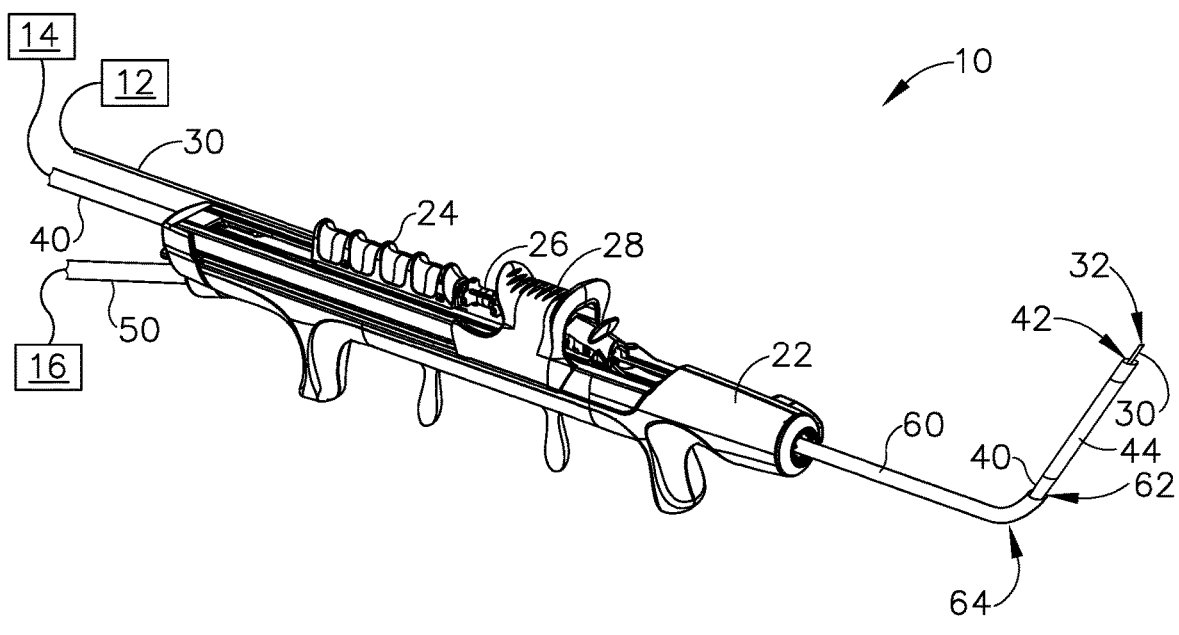
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
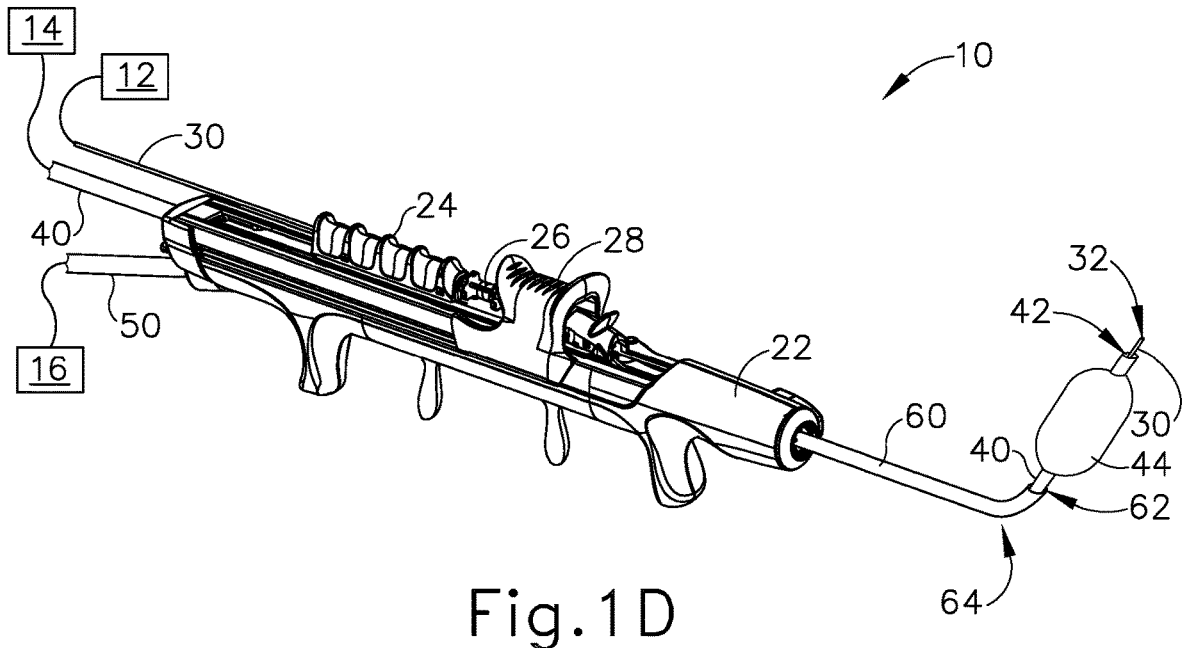
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to an open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pat. No. 9,962,530, entitled "Inflator for Dilation of Anatomical Passageway," issued on May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra™ Sinus Balloon Catheter by Acclarent, Inc. of Irvine, California. In some other versions, dilator catheter (40) is configured and operable similar to the Relieva Solo Pro™ Sinus Balloon Catheter by Acclarent, Inc. of Irvine, California Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passage-way associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, California Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, California.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, the disclosure of which is incorporated by reference herein. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, the disclosure of which is incorporated by reference herein. As another merely illustrative example, versions of dilation instrument (20) that include a malleable guide member may be constructed and operable in accordance with at least some of the teachings of U.S. Pub. No. 2017/0120020, entitled "Apparatus for Bending Malleable Guide of Surgical Instrument," published May 4, 2017, the disclosure of which is incorporated by reference herein; and/or U.S. Pub. No. 2012/0071857, entitled "Methods and Apparatus for Treating Disorders of the Sinuses," published Mar. 22, 2012, the disclosure of which is incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, the disclosure of which is incorporated by reference herein. Other suitable kinds of endoscopes that may be used with the various versions of dilation instrument assembly (10) described herein will be apparent to those of ordinary skill in the art.

II. Exemplary Guidance of Dilation Catheter System

A. Image Guided Surgery Navigation System

Figures 2, 3:
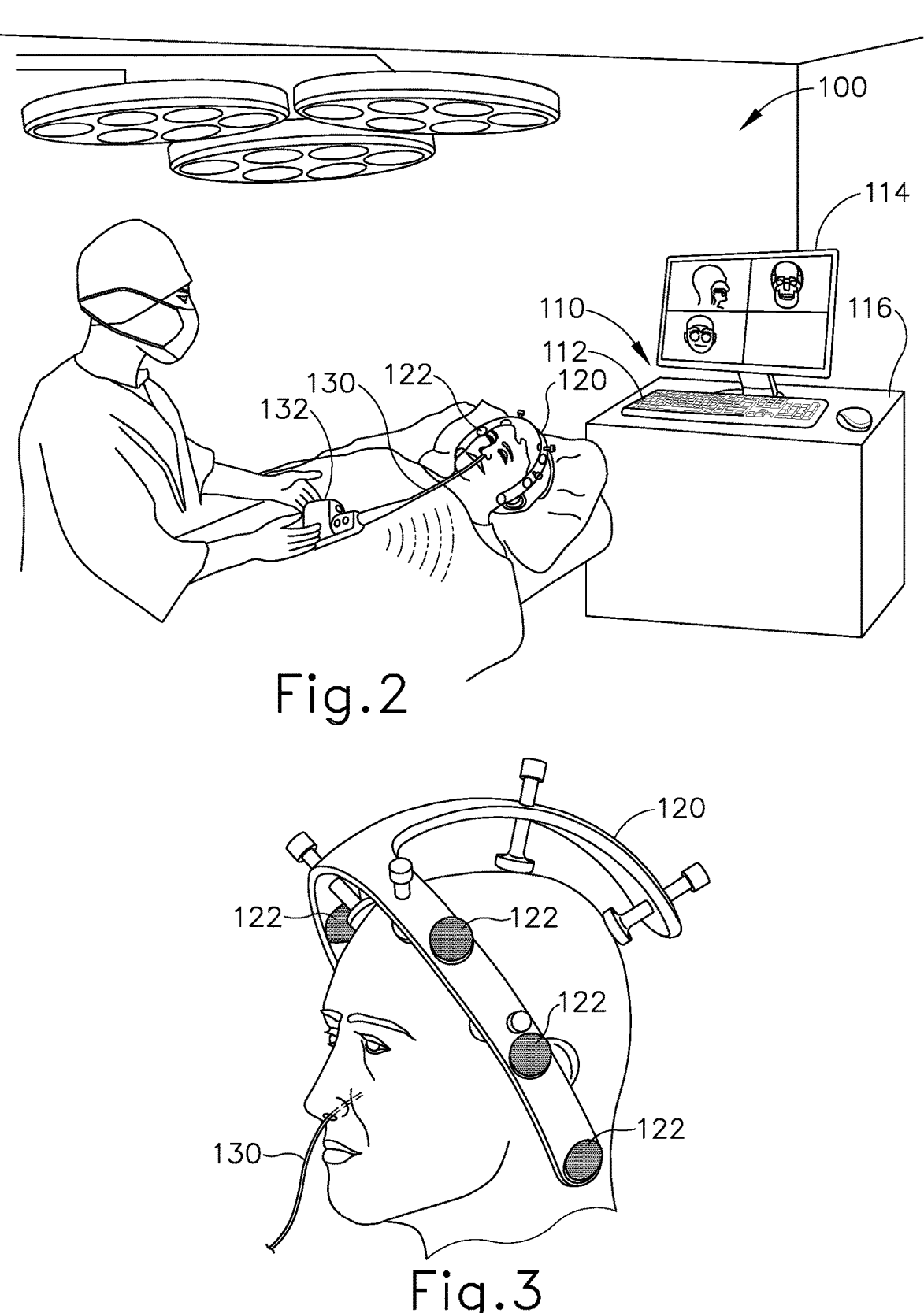
FIG. 2 depicts a schematic view of an exemplary image guided surgery (IGS) navigation system for use with the dilation instrument assembly of FIG. 1A.
FIG. 3 depicts a perspective view of the head of a patient, with components of the navigation system of FIG. 2.

FIG. 2 shows an exemplary IGS navigation system (100) whereby an ENT procedure may be performed using IGS. In some instances, IGS navigation system (100) is used during a procedure where dilation instrument assembly (10) that may be used to dilate the ostium of a paranasal sinus; or to dilate some other anatomical passageway (e.g., within the ear, nose, or throat, etc.). However, it should be understood that IGS navigation system (100) may be readily used in various other kinds of procedures.

In addition to or in lieu of having the components and operability described herein, IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, the disclosure of which is incorporated by reference herein; U.S. Pat. Pub. No. 2014/0200444, entitled "Guidewires for Performing Image Guided Procedures," published Jul. 17, 2014, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, the disclosure of which is incorporated by reference herein.

IGS navigation system (100) of the present example comprises a set of magnetic field generators (122). Before a surgical procedure begins, field generators (122) are fixed to the head of the patient. As best seen in FIG. 3, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (30) described above, and may include a sensor (not shown) that is responsive to movement within the fields generated by field generators (122). In particular, with respect to FIG. 2, signals generated by the sensor of navigation guidewire (130) may be processed by a processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of IGS navigation system (100). It should be understood that, when used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130).

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 2 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and a driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (100) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

B. Illumination Guidance System

Figures 4, 5, 6:
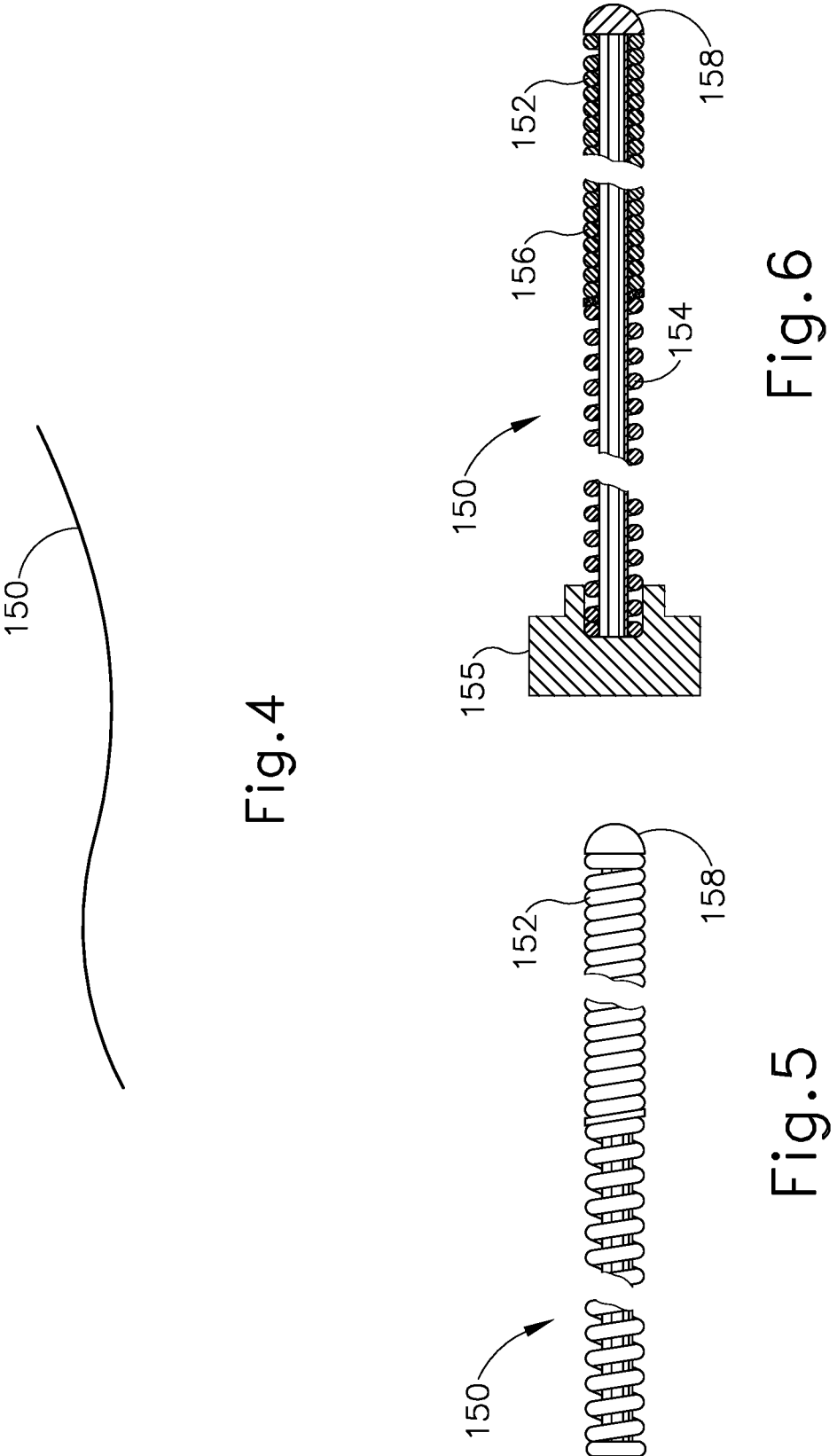
FIG. 4 depicts a side elevational view of an exemplary illuminating guidewire for use in the dilation instrument assembly of FIG. 1A.
FIG. 5 depicts an enlarged side elevational view of the illuminating guidewire of FIG. 4.
FIG. 6 depicts an enlarged side cross-sectional view of the illuminating guidewire of FIG. 4 taken along a centerline thereof.

As shown in FIGS. 4-6, an exemplary illuminating guidewire (150) includes a coil (152) positioned about a core wire (154). An illumination fiber (156) extends along the interior of core wire (154) and terminates in an atraumatic lens (158). A connector (155) at a proximal end of illuminating guidewire (150) enables optical coupling between illumination fiber (156) and a light source (not shown). Illumination fiber (156) may comprise one or more optical fibers. Lens (158) is configured to project light when illumination fiber (156) is illuminated by the light source, such that illumination fiber (156) transmits light from the light source to the lens (158). In some versions, a distal end of illuminating guidewire (150) is more flexible than the proximal end of illuminating guidewire (150). Illuminating guidewire (150) has a length enabling the distal end of illuminating guidewire (150) to be positioned distal to balloon (44) (see FIG. 1D) while the proximal end of illuminating guidewire (150) is positioned proximal to handle body (22) (see FIG. 1D). Illuminating guidewire (150) may include indicia along at least part of its length (e.g., the proximal portion) to provide the operator with visual feedback indicating the depth of insertion of illuminating guidewire (150) relative to dilation catheter (40) (see 1D). By way of example only, illuminating guidewire (150) may be configured in accordance with at least some of the teachings of U.S. Pat. No. 9,155,492, the disclosure of which is incorporated by reference herein. In some versions, illuminating guidewire (150) is configured similar to the Relieva Luma Sentry™ Sinus Illumination System by Acclarent, Inc. of Irvine, California Other suitable forms that illuminating guidewire (150) may take will be apparent to those of ordinary skill in the art in view of the teachings herein.

III. Exemplary Guidewire with Core Wire Sleeve

Figure 7:
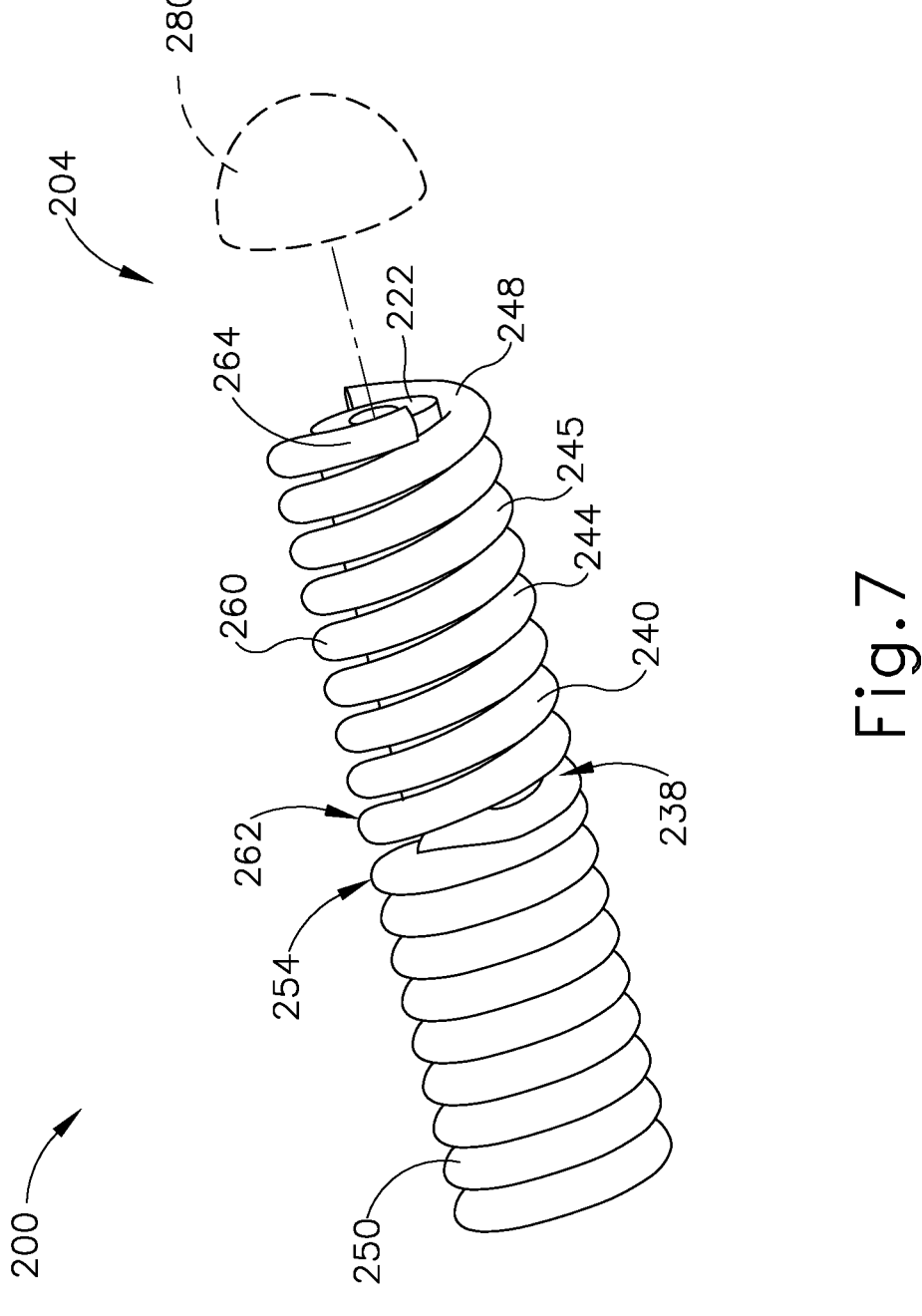
FIG. 7 depicts an enlarged, partially exploded perspective view of a distal portion of a first exemplary intertwined guidewire for use in the dilation instrument assembly of FIG. 1A.

FIG. 7 shows a first exemplary intertwined guidewire (200) that may be incorporated into dilation instrument assembly (10) in place of guidewire (30, 130, 150) and provide for simpler manufacture of a core wire assembly (238). In some versions, at least a portion of the length of guidewire (200) (e.g., approximately 7 inches) is coated in one or more materials. By way of example only, at least a portion of the length of guidewire (200) may be coated in silicone. Other suitable materials that may be used as a coating for guidewire (200) will be apparent to those of ordinary skill in the art in view of the teachings herein. Except as otherwise described below, guidewire (200) is configured and operable similar to any one or more of the various guidewires (30, 130, 150) described above. Guidewire (200) may thus be configured to provide IGS navigation system (100) compatibility or illumination guidance system compatibility to dilation instrument assembly (10).

Figure 8:
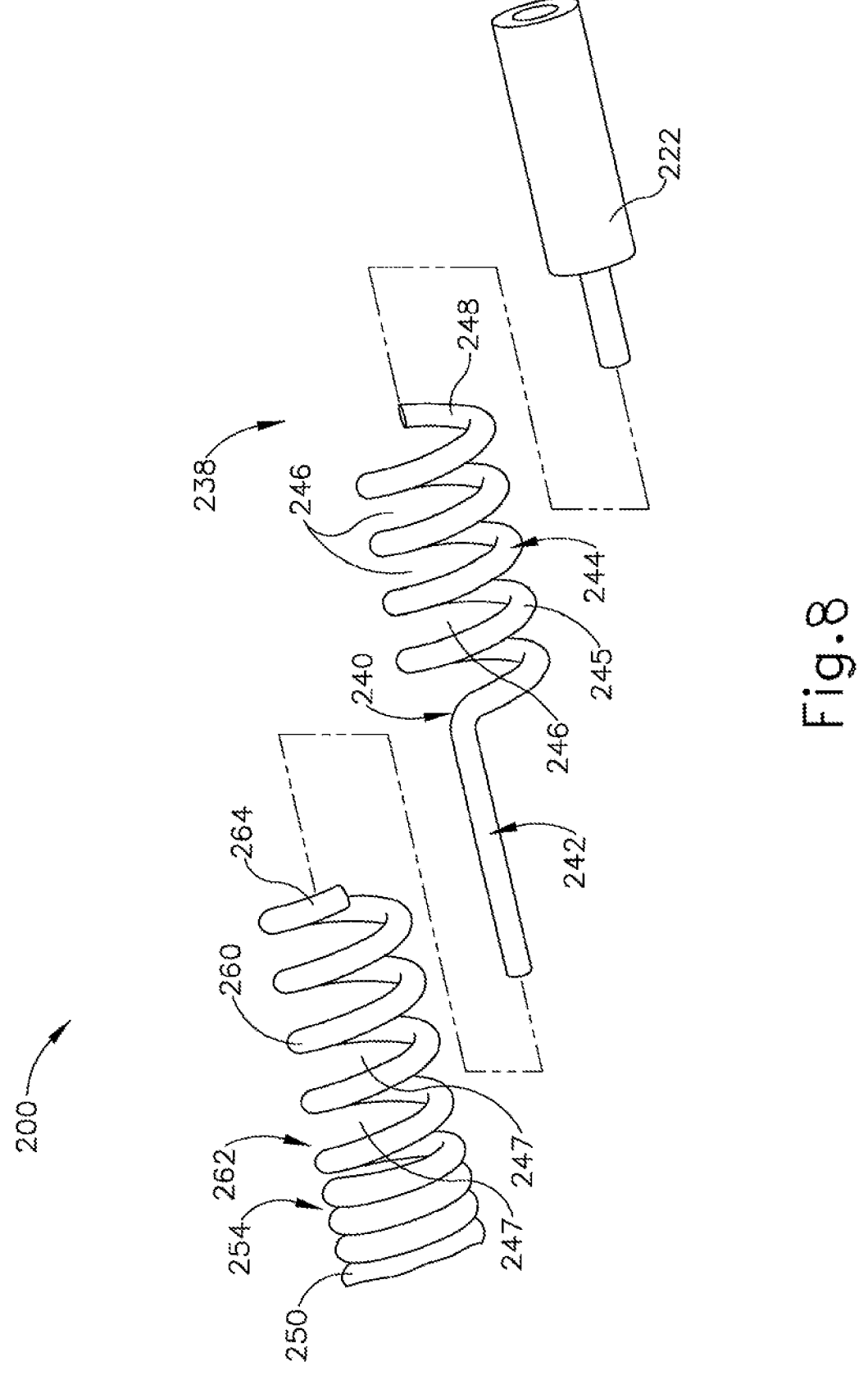
FIG. 8 depicts an enlarged, exploded perspective view of the intertwined guidewire of FIG. 7.

Guidewire (200) of the present example has a proximal end (not shown), a distal end (204), and an intermediate region (not shown) extending therebetween. Proximal end (not shown) and intermediate region (not shown) are generally constructed as discussed above in other examples provided herein. As best seen in FIGS. 7-8, guidewire (200) includes a proximal coil (250) of helical wire, a distal coil (260) of helical wire, and intertwined core wire assembly (238). A proximal end (not shown) of proximal coil (250) proximally terminates in a solder joint (not shown), which joins a tubular member (not shown) with proximal coil (250). Proximal coil (250) helically extends distally from this solder joint to a distal end (254) of proximal coil (250) and engages with distal coil (260). Proximal end (262) of distal coil (260) is joined with distal end (254) of proximal coil (250). In some examples, proximal coil (250) may include a preformed bend (not shown) formed between proximal end (not shown) and distal end (254). Bend (not shown) may be bent at an angle in accordance with bend angles known in the art of guidewires that are used in ENT surgical procedures.

In some versions, coils (250, 260) are formed from a single, monolithic piece of wire, such that distal end (254) of proximal coil (250) continuously transitions to proximal end (262) of distal coil (260), such that coils (250, 260) form a single, homogenous continuum of material. Thus, use of terms "proximal coil (250)" and "distal coil (260)" should not be read as necessarily requiring that proximal coil (250) be formed separately from distal coil (260), with coils (250, 260) being subsequently joined together (though such a process may be used in some variations).

In some other versions, ends (254, 262) are joined together in an interlocking fashion, such that the overlapping regions of coils (250, 260) form a double helix. More particularly, coils (250, 260) coaxially align along a longitudinal coil axis, which may be straight or bent as discussed above. By way of example only, the interlocking regions of ends (254, 262) may extend along approximately one to two full coil wraps of coils (250, 260). By way of further example only, the interlocking regions of ends (254, 262) may extend along a length between approximately 0.5 mm and approximately 0.75 mm. In the present example, proximal and distal coils (250, 260) are formed of metallic wires (e.g., stainless steel) wrapped in a helical configuration. Also in the present example, a ring of solder (not shown) is applied to the interlocking regions of coils (250, 260) to further secure the interlocking regions of coils (250, 260) together. By way of example only, ring of solder (not shown) may be formed of tin-silver solder. Alternatively, any other suitable material(s) may be used.

In the present example, coils (250, 260) have the same outer diameter but different inner diameters. By way of example only, coils (250, 260) may both have an outer helical diameter of approximately 0.0345 inches. Alternatively, any other suitable diameters may be used. Also in the present example, proximal coil (250) has a length of approximately 4.5 inches; while distal coil (260) has a length of approximately 4.25 mm. Alternatively, coils (250, 260) may have any other suitable lengths. Also in the present example, proximal coil (250) has an open pitch of approximately 0.75 mm, in which the open pitch of distal coil (260) is interlocked with a corresponding open pitch, though any other suitable pitch may be used. By way of further example only, the above-noted features of guidewire (200) may be constructed an operable in accordance with at least some of the teachings of U.S. patent application Ser. No. 15/861,959, entitled "Navigation Guidewire with Interlocked Coils," filed Jan. 4, 2018, the disclosure of which is incorporated by reference herein. In versions where coils (250, 260) consist of a single, monolithic, homogenous continuum of material, coils (250, 260) may define the same outer diameter and the same inner diameter.

A tip member (280) is secured to a distal end (264) of distal coil (260). Tip member (280) has an atraumatic, dome shape in the present example. In some versions, tip member (280) is formed by adhesive. In some other versions, tip member (280) is formed as a separate piece (e.g., of a polymer) and is then secured to distal end (264), secured to adhesive, or secured to a sensor (222) and ferrite. Sensor (222) is configured to generate electrical signals in response to movement within an electromagnetic field, such that sensor (222) enables guidewire (200) to provide navigation capabilities with a system like IGS navigation system (100). An alternative tip member may contain a lens and/or light fibers for an alternative guide system such as those discussed above. Other suitable ways in which tip member (280) may be formed and secured will be apparent to those of ordinary skill in the art in view of the teachings herein. Examples of adhesive include, but are not limited to, epoxy, acrylic, polyurethane, and/or cyanoacrylate for bonding various components and to form the lens and/or atraumatic tip member (280).

Intertwined core wire assembly (238) is attached within proximal and distal coils (250, 260) and is configured to inhibit longitudinal elongation of the proximal and distal coils (250, 260) along the longitudinal coil axis. To this end, intertwined core wire assembly (238) has a core wire (240) with a proximal elongate portion (242) extending to a distal spiral portion (244). Proximal elongate portion (242) of core wire (240) extends generally parallel with and offset from the longitudinal coil axis and is proximally secured to tubular member (not shown) within guidewire (200), thereby providing a mechanical ground. Proximal elongate portion (242) extends distally from this tubular member and through proximal coil (250) to distal spiral portion (244), which engages with distal coil (260) for inhibiting relative movement therebetween for assembly as discussed below in greater detail.

Core wire (240) is formed of a non-extensible material that provides strength to the region of guidewire (200) along which core wire (240) extends. In particular, core wire (240) inhibits guidewire (200) from stretching longitudinally along the longitudinal coil axis. While core wire (240) is non-extensible in this example, core wire (240) is flexible. Moreover, other than the proximal and distal ends of intertwined core wire assembly (238), the intermediate region of intertwined core wire assembly (238) is not fixedly secured within guidewire (200). Thus, intertwined core wire assembly (240) does not adversely affect the lateral flexibility of guidewire (200). By way of example only, the proximal end of core wire (240) may be secured to the inner wall of the tubular member (or some other feature of guidewire (200)) via an adhesive, via an epoxy, or using any other suitable means or techniques as will be apparent to those of ordinary skill in the art in view of the teachings herein.

Figure 9:
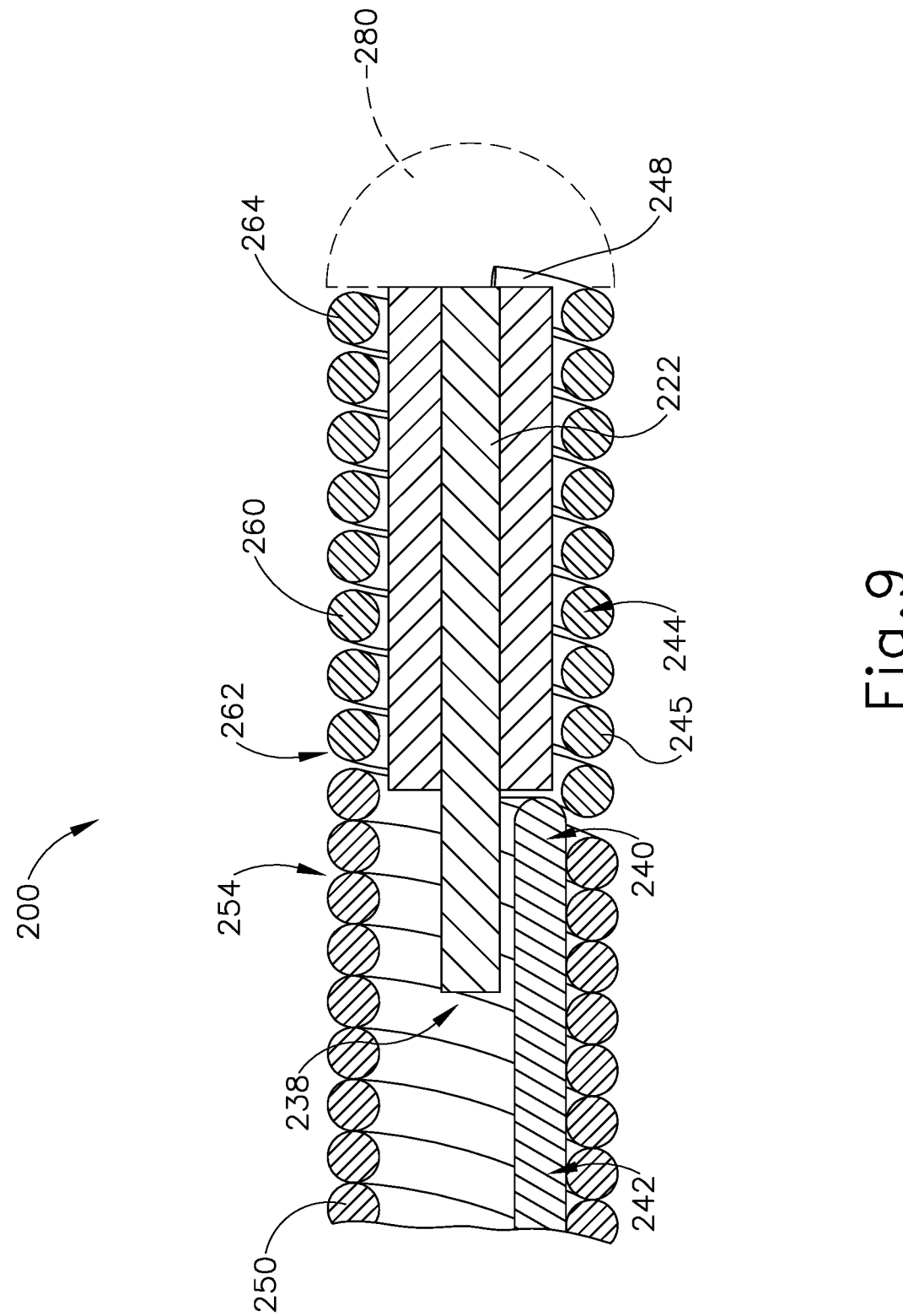
FIG. 9 depicts an enlarged cross-sectional view of the intertwined guidewire of FIG. 7 taken along a centerline thereof.

In the present example shown in FIGS. 8-9, distal spiral portion (244) of core wire (240) includes a helical wire coil (245) spiraling about the longitudinal coil axis with a preformed pitch and defining a helical space (246). Similarly, distal coil (260) spirals about the longitudinal coil axis with the preformed pitch defining another helical space (247). Helical wire coil (245) is wound about distal coil (260) such that helical space (247) of distal coil (260) receives wire coil (245) and, in turn, helical space (246) of helical wire coil (245) receives distal coil (260). Helical wire coil (245) is thereby intertwined with distal coil (260). Furthermore, helical wire coil (245) and distal coil (260) have generally equivalent outer and inner helical diameters about the longitudinal coil axis and engage each other while intertwined. Helical wire coil (245) thus longitudinally overlaps with distal coil (260) to inhibit longitudinal movement therebetween and frictionally engages distal coil (260) to inhibit rotational movement therebetween. Such intertwinement in the present example thereby inhibits relative movement to provide simpler assembly of helical wire coil (245) and distal coil (260) for use. For example, one or more portions of helical wire coil (245), such as a distal end (248), are directly and fixedly secured to respective portions of distal coil (260) by an adhesive while intertwinement holds helical wire coil (245) stationary relative to distal coil (260). Alternatively or in addition to adhesive, helical wire coil (245) and distal coil (260) may be laser welded, resistance welded, TIG welded, or spot welded.

Helical wire coil (245) of the present example has approximately 4.5 spiraled coils, which may also be referred to as turns, about the longitudinal coil axis, thereby defining a helix. Generally, more spiraled coils provide for more engagement between helical wire coil (245) and distal coil (260), whereas fewer spiraled coils provide for less engagement between helical wire coil (245) and distal coil (260). It will be appreciated that any number of such spiraled coils may be used, and the invention is not intended to be unnecessarily limited to helical wire coil (245) shown and described herein. For example, an alternative wire coil may define only a portion of a helix rather than an entire helix as shown with respect to helical wire coil (245). In addition, proximal elongate portion (242) of core wire (250) in the present example is positioned radially inward of the inner helical diameter to extend along an interior surface of proximal coil (250). It will be appreciated that proximal elongate portion (242) may be alternatively positioned within proximal coil (250) in other examples also in accordance with the invention described herein.

In manufacture, elongate portion (242) of core wire (240) is inserted through proximal coil (242) to position helical wire coil (245) of core wire (240) adjacent to distal coil (260). Helical wire coil (245), which is pre-formed in the present example, is then wound about distal coil (260) such that helical wire coil (245) is received within helical space (247) of distal coil (260). Alternatively, helical wire coil (245) may be formed while being wound about distal coil (260). In either case, helical wire coil (245) is intertwined with distal coil (260) to inhibit relative movement therebetween in order to fixedly secure helical wire coil (245) to distal coil (260) for use as discussed above.

Figure 10:
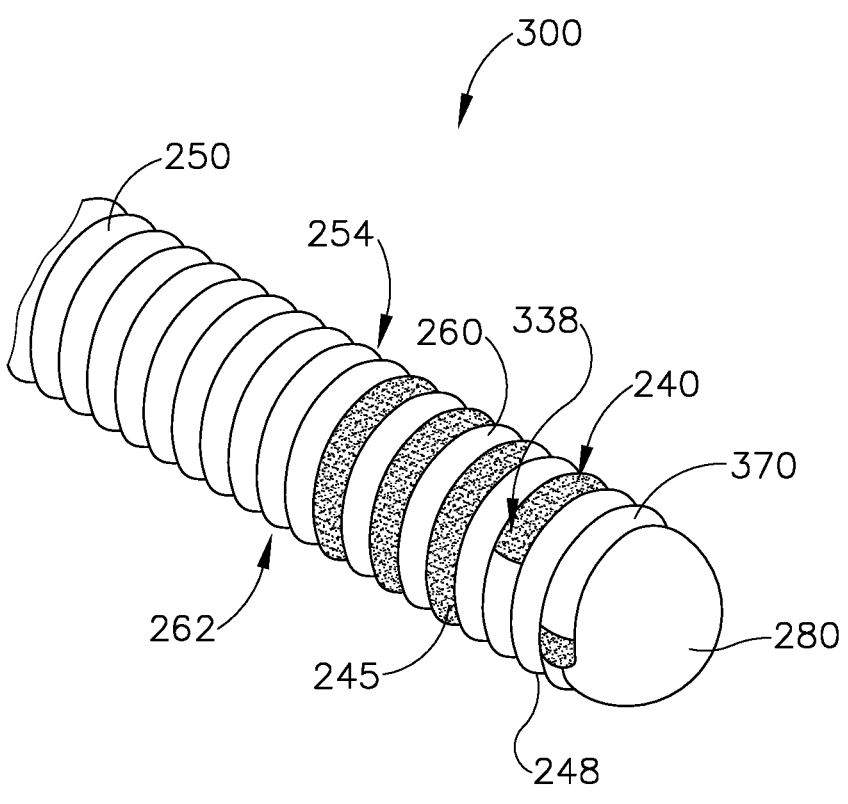
FIG. 10 depicts an enlarged perspective view of a distal portion of a second exemplary intertwined guidewire with a helical sleeve for use in the dilation instrument assembly of FIG. 1A.
Figure 11:
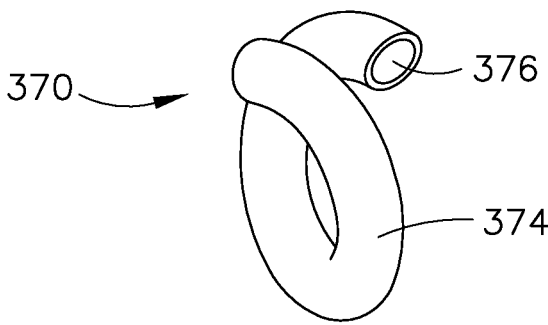
FIG. 11 depicts a perspective view of the helical sleeve of FIG. 10.

FIGS. 10-11 illustrate a second exemplary intertwined guidewire (300) with an intertwined core wire assembly (338) similar to intertwined core wire assembly (238) (see FIG. 7) with core wire (240) fixedly secured relative to distal coil (260). However, rather than distal end (248) of core wire (240) being affixed directly to distal coil (260) as discussed above, distal end (248) of core wire (240) is secured within a helical sleeve (370), which, in turn, is attached to distal coil (260). In the present example, sleeve (370) is a flexible tube (374) defining a helical bore (376) formed from a material configured to be attached to distal coil (260), such as by welding, soldering, or brazing. Core wire (240) may thus be selected from available materials to be non-extensible without regard for attachability to distal coil (260), whereas sleeve (270) may be selected from available materials for attachability to distal coil (260) without regard for non-extensibility. Helical sleeve (370) is thus formed from a material different than the material that forms core wire (240).

By way of example only, helical sleeve (370) may be formed from stainless steel, a nickel titanium alloy, tantalum, niobium, or other metallic material capable of being welded, soldered, or brazed. By way of further example only, core wire (240) may formed from nitinol, nitinol-cobalt, or other material that is non-extensible. While the present example of helical sleeve (370) is flexible tube (374), it will be appreciated that alternative structures may surround core wire (240), in whole or in part, to form helical sleeve (370). For example, an alternative sleeve may be formed from wire wrapped about core wire (240) to define an alternative bore. Helical sleeve (370) is thus not intended to be unnecessarily limited to flexible tube (374). Moreover, in some variations, sleeve (370) is formed from a rigid material. Further details regarding securement of alternative sleeves are described in U.S. patent application Ser. No. 15/686,796, entitled "Core Wire Assembly for Guidewire," filed Aug. 25, 2017, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, comprising: (a) a first helical wire coil; and (b) a core wire having a first wire portion and a second wire portion, wherein the first wire portion of the core wire extends through the first helical wire coil, wherein the second wire portion of the core wire is intertwined with the first helical wire coil to fixedly secure the core wire relative to the first helical wire coil, wherein the core wire is formed from a first material that is non-extensible, wherein the core wire is fixedly secured relative to a distal portion of the first helical wire coil such that the core wire inhibits longitudinal elongation of the first helical wire coil along a longitudinal coil axis.

EXAMPLE 2

The apparatus of Example 1, wherein the core wire is engaged with the first helical wire coil to inhibit relative movement therebetween for securement.

EXAMPLE 3

The apparatus of any one or more of Examples 1 through 2, wherein the first helical wire coil defines a helical space, and wherein the core wire is intertwined with the first helical wire coil such that the core wire is received within the helical space.

EXAMPLE 4

The apparatus of any one or more of Examples 1 through 3, wherein the second portion of the core wire has a second helical wire coil, and wherein the second helical wire coil defines at least a portion of a helix and is intertwined with the first helical wire coil.

EXAMPLE 5

The apparatus of Example 4, wherein the first helical wire coil defines a helical space, and wherein the second helical wire coil is intertwined with the first helical wire coil such that the second helical wire coil is received within the helical space.

EXAMPLE 6

The apparatus of Example 5, wherein the first helical wire coil has a first helical pitch and the second helical wire coil has a second helical pitch, and wherein the first and second helical pitches are generally equivalent.

EXAMPLE 7

The apparatus of Example 6, wherein the first helical wire coil defines a first outer helical diameter and the second helical wire coil defines a second outer helical diameter, and wherein the first and second outer helical diameters are generally equivalent.

EXAMPLE 8

The apparatus of any one or more of Examples 5 through 7, wherein the second helical wire coil is engaged with the first helical wire coil to inhibit relative movement therebetween for securement.

EXAMPLE 9

The apparatus of Example 8, wherein the second helical wire coil is engaged with the first helical wire coil to inhibit relative longitudinal movement therebetween.

EXAMPLE 10

The apparatus of Example 9, wherein the second helical wire coil is engaged with the first helical wire coil to inhibit relative rotational movement therebetween.

EXAMPLE 11

The apparatus of any one or more of Examples 1 through 10, wherein the core wire is fixedly secured to the distal portion of the first helical wire coil such that core wire inhibits longitudinal elongation of the first helical wire coil along the longitudinal coil axis.

EXAMPLE 12

The apparatus of Example 11, wherein the core wire is fixedly secured to the distal portion of the first helical wire coil with an adhesive.

EXAMPLE 13

The apparatus of any one or more of Examples 1 through 12, further comprising a helical sleeve having a helical bore, wherein at least a portion of the core wire is disposed within the helical bore of the helical sleeve, wherein the core wire is secured within the helical sleeve, wherein the helical sleeve is formed from a second material, wherein the second material of the helical sleeve is different than the first material of the core wire, wherein the sleeve is fixedly secured to the distal portion of the first helical wire coil such that core wire inhibits longitudinal elongation of the first helical wire coil along the longitudinal coil axis.

EXAMPLE 14

The apparatus of Example 13, wherein the first material and the second material are configured to be brazed, soldered, or welded together.

EXAMPLE 15

The apparatus of any one or more of Examples 1 through 14, further comprising: (a) a body; (b) a guide extending distally from the body; (c) a guidewire including the first helical wire coil and the core wire, wherein the guidewire is slidably disposed relative to the guide; and (d) a dilation catheter slidably disposed relative to the guidewire, wherein the dilation catheter includes an expandable dilator.

EXAMPLE 16

An apparatus, comprising: (a) a proximal wire coil, wherein the proximal wire coil is helical; (b) a distal wire coil, wherein the distal wire coil is helical and interlocked with the proximal wire coil such that the proximal and distal wire coils form a double helix configuration extending along a longitudinal coil axis, wherein the distal wire coil defines a helical space; and (c) a core wire having a first wire portion and a second wire portion, wherein the first wire portion of the core wire extends through the proximal wire coil, wherein the second wire portion of the core wire has a core helical wire coil intertwined with the distal wire coil such that the core helical wire is received within the helical space and engaged with the distal wire coil to inhibit movement of the core helical wire relative to the distal wire coil and fixedly secure the core wire relative to the distal wire coil, wherein the core wire is formed from a first material that is non-extensible, wherein the core helical wire coil is fixedly secured relative to a distal portion of the distal wire coil such that the core wire inhibits longitudinal elongation of the proximal and distal wire coils along a longitudinal coil axis.

EXAMPLE 17

The apparatus of Example 16, wherein the core wire is fixedly secured to the distal portion of the distal wire coil such that core wire inhibits longitudinal elongation of the proximal and distal wire coils along the longitudinal coil axis.

EXAMPLE 18

The apparatus of any one or more of Examples 16 through 17, further comprising a helical sleeve having a helical bore, wherein the core helical wire coil of the core wire is disposed within the helical bore of the helical sleeve, wherein the core helical wire coil is secured within the helical sleeve, wherein the helical sleeve is formed from a second material, wherein the second material of the helical sleeve is different than the first material of the core wire, wherein the sleeve is fixedly secured to the distal portion of the distal wire coil such that core wire inhibits longitudinal elongation of the proximal and distal wire coils along the longitudinal coil axis.

EXAMPLE 19

The apparatus of any one or more of Examples 16 through 18, further comprising: (a) a body; (b) a guide extending distally from the body; (c) a guidewire including the distal wire coil, the proximal wire coil, and the core wire, wherein the guidewire is slidably disposed relative to the guide; and (d) a dilation catheter slidably disposed relative to the guidewire, wherein the dilation catheter includes an expandable dilator.

EXAMPLE 20

A method of manufacturing a guidewire for a dilation catheter, the method comprising: (a) inserting a first portion of a core wire through a helical wire coil; (b) intertwining a second portion of the core wire with the helical wire coil to engage the second portion of the core wire with the helical wire coil and thereby inhibit relative movement therebetween; and (c) fixedly securing the core wire relative to the helical wire coil, wherein the core wire inhibits elongation of the helical wire coil, and wherein the core wire permits lateral deformation of the helical wire coil.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   a first helical wire coil having a first outer diameter; and
   a core wire having a first wire portion and a second wire portion, wherein the first wire portion of the core wire extends through the first helical wire coil, wherein the second wire portion of the core wire comprises a second helical wire coil having a second outer diameter that is configured such that the second helical wire coil is radially intertwined with the first helical wire coil to fixedly secure the core wire relative to the first helical wire coil, wherein the core wire is formed from a first material that is non-extensible,
   wherein the core wire is fixedly secured relative to a distal portion of the first helical wire coil such that the core wire inhibits longitudinal elongation of the first helical wire coil along a longitudinal coil axis.

2. The apparatus of claim 1, wherein the core wire is engaged with the first helical wire coil to inhibit relative movement therebetween for securement.

3. The apparatus of claim 1, wherein the first helical wire coil defines a helical space, and wherein the core wire is intertwined with the first helical wire coil such that the core wire is received within the helical space.

4. The apparatus of claim 1, wherein the second wire portion of the core wire has a second helical wire coil, and wherein the second helical wire coil defines at least a portion of a helix and is intertwined with the first helical wire coil.

5. The apparatus of claim 4, wherein the first helical wire coil defines a helical space, and wherein the second helical wire coil is intertwined with the first helical wire coil such that the second helical wire coil is received within the helical space.

6. The apparatus of claim 5, wherein the first helical wire coil has a first helical pitch and the second helical wire coil has a second helical pitch, and wherein the first helical pitch and the second helical pitch are equivalent.

7. The apparatus of claim 6, wherein the first helical wire coil defines a first outer helical diameter and the second helical wire coil defines a second outer helical diameter, and wherein the first helical diameter and the second outer helical diameter are equivalent.

8. The apparatus of claim 5, wherein the second helical wire coil is engaged with the first helical wire coil to inhibit relative movement therebetween for securement.

9. The apparatus of claim 8, wherein the second helical wire coil is engaged with the first helical wire coil to inhibit relative longitudinal movement therebetween.

10. The apparatus of claim 9, wherein the second helical wire coil is engaged with the first helical wire coil to inhibit relative rotational movement therebetween.

11. The apparatus of claim 1, wherein the core wire is fixedly secured to the distal portion of the first helical wire coil such that core wire inhibits longitudinal elongation of the first helical wire coil along the longitudinal coil axis.

12. The apparatus of claim 11, wherein the core wire is fixedly secured to the distal portion of the first helical wire coil with an adhesive.

13. The apparatus of claim 1, further comprising a helical sleeve having a helical bore, wherein at least a portion of the core wire is disposed within the helical bore of the helical sleeve, wherein the core wire is secured within the helical sleeve, wherein the helical sleeve is formed from a second material, wherein the second material of the helical sleeve is different than the first material of the core wire, wherein the helical sleeve is fixedly secured to the distal portion of the first helical wire coil such that core wire inhibits longitudinal elongation of the first helical wire coil along the longitudinal coil axis.

14. The apparatus of claim 13, wherein the first material and the second material are configured to be brazed, soldered, or welded together.

15. The apparatus of claim 1, further comprising:

(a) a body;

(b) a guide extending distally from the body;

(c) a guidewire including the first helical wire coil and the core wire, wherein the guidewire is slidably disposed relative to the guide; and (d) a dilation catheter slidably disposed relative to the guidewire, wherein the dilation catheter includes an expandable dilator.

16. An apparatus, comprising:

a proximal wire coil, wherein the proximal wire coil is helical;

a distal wire coil, wherein the distal wire coil is helical and interlocked with the proximal wire coil such that the proximal and distal wire coils form a double helix configuration extending along a longitudinal coil axis, wherein the distal wire coil defines a helical space; and a core wire having a first wire portion and a second wire portion, wherein the first wire portion of the core wire extends through the proximal wire coil, wherein the second wire portion of the core wire has a core helical wire coil having a second outer diameter that is configured such that the core helical wire coil is radially intertwined in the helical space with the distal wire coil such that the core helical wire coil is received within the helical space and engaged with the distal wire coil to inhibit movement of the core helical wire coil relative to the distal wire coil and fixedly secure the core wire relative to the distal wire coil, wherein the core wire is formed from a first material that is non-extensible, wherein the core helical wire coil is fixedly secured relative to a distal portion of the distal wire coil such that the core wire inhibits longitudinal elongation of the proximal wire coil and the distal wire coil along a longitudinal coil axis.

17. The apparatus of claim 16, wherein the core wire is fixedly secured to the distal portion of the distal wire coil such that core wire inhibits longitudinal elongation of the proximal and distal wire coils along the longitudinal coil axis.

18. The apparatus of claim 16, further comprising a helical sleeve having a helical bore, wherein the core helical wire coil of the core wire is disposed within the helical bore of the helical sleeve, wherein the core helical wire coil is secured within the helical sleeve, wherein the helical sleeve is formed from a second material, wherein the second material of the helical sleeve is different than the first material of the core wire, wherein the helical sleeve is fixedly secured to the distal portion of the distal wire coil such that core wire inhibits longitudinal elongation of the proximal wire coil and the distal wire coil along the longitudinal coil axis.

19. The apparatus of claim 16, further comprising:

(a) a body;

(b) a guide extending distally from the body;

(c) a guidewire including the distal wire coil, the proximal wire coil, and the core wire, wherein the guidewire is slidably disposed relative to the guide; and (d) a dilation catheter slidably disposed relative to the guidewire, wherein the dilation catheter includes an expandable dilator.

20. The apparatus of claim 1, wherein the second outer diameter is equivalent to the first outer diameter.

* * * * *